(12) United States Patent
Solar et al.

(10) Patent No.: US 7,695,480 B2
(45) Date of Patent: Apr. 13, 2010

(54) BALL AND SOCKET TRAJECTORY GUIDE

(75) Inventors: Matthew S. Solar, Indialantic, FL (US);
James G. Skakoon, St. Paul, MN (US);
Kari Parmer, Brooklyn Park, MN (US);
Thomas I. Miller, Palm Bay, FL (US);
Mark Stephen Freas, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 797 days.

(21) Appl. No.: 10/671,913

(22) Filed: Sep. 25, 2003

(65) Prior Publication Data

US 2005/0070920 A1    Mar. 31, 2005

(51) Int. Cl.
*A61B 19/00*    (2006.01)
(52) U.S. Cl. ..................................... 606/130
(58) Field of Classification Search ................. 606/129, 606/130, 96, 98, 166; 403/122; 600/184–200
See application file for complete search history.

(56) References Cited

U.S. PATENT DOCUMENTS

| 3,073,310 | A | * | 1/1963 | Mocarski ..................... 606/130 |
| 3,457,922 | A | * | 7/1969 | Ray ............................ 606/130 |
| 4,613,324 | A | | 9/1986 | Ghajar |
| 4,998,938 | A | * | 3/1991 | Ghajar et al. ............... 606/130 |
| 5,235,988 | A | | 8/1993 | Johnson et al. |
| 5,263,956 | A | | 11/1993 | Nobles |
| 5,423,826 | A | * | 6/1995 | Coates et al. ................ 606/96 |
| 5,752,962 | A | * | 5/1998 | D'Urso ....................... 606/130 |
| 5,776,143 | A | | 7/1998 | Adams |
| 5,957,927 | A | * | 9/1999 | Magee et al. ................. 606/99 |
| 6,110,182 | A | * | 8/2000 | Mowlai-Ashtiani .......... 606/130 |
| 6,267,769 | B1 | | 7/2001 | Truwit ........................ 606/130 |
| 6,328,748 | B1 | * | 12/2001 | Hennig ...................... 606/130 |
| 6,368,329 | B1 | | 4/2002 | Truwit |
| 2002/0042605 | A1 | | 4/2002 | Castaneda et al. |
| 2003/0055436 | A1 | | 3/2003 | Daum et al. |
| 2003/0114752 | A1 | * | 6/2003 | Henderson et al. .......... 600/433 |

FOREIGN PATENT DOCUMENTS

| DE | 1949923 | 4/1971 |
| DE | 4409833 A1 | 10/1995 |
| JP | 2003126107 | 5/2003 |
| WO | WO 01/49197 A1 | 7/2001 |
| WO | WO 2005030075 A2 | 4/2005 |

OTHER PUBLICATIONS

"International Search Report and Written Opinion, Application No. PCT/US2004/031109, date mailed May 27, 2005", 17 Pages.
"Invitation to pay additional Fees, Application No. PCT/US2004/031109, date mailed Jan. 26, 2005", 6 Pages.

* cited by examiner

*Primary Examiner*—(Jackie) Tan-Uyen T. Ho
*Assistant Examiner*—Melanie Tyson
(74) *Attorney, Agent, or Firm*—Harness, Dickey

(57) ABSTRACT

An alignment device and method is provided. Higher precision is achieved when fixing an orientation of an insertion axis using alignment devices shown. A symmetric clamping force is provided that reduces or eliminates unwanted displacement after the desired orientation is obtained. Another feature includes increased flexibility to use a variety of primary medical devices. Another feature includes a standoff feature that reduces tissue damage. Another feature includes an orienting fixture for image guided procedures.

34 Claims, 10 Drawing Sheets

BALL AND SOCKET TRAJECTORY GUIDE

FIELD OF THE INVENTION

This application relates to alignment devices. Specifically, but not by way of limitation, this application relates to aligning medical devices for an insertion procedure into a subject.

BACKGROUND

Using a medical application as an example, a primary medical device is positioned, and inserted into a location within a subject. When introducing a primary medical device into a patient, one type of procedure utilizes an assembly of additional devices that interact with the primary medical device to aid in precision introduction of the primary medical device.

An example of a primary medical device includes an elongated structure, such as a catheter, designed to function with one end inside the patient, and operational control external to the patient. The primary medical device includes an active portion attached to a distal end that may include, but is not limited to: a biopsy probe; drug delivery capability; a tissue removal instrument such as a laser; an instrument for placing an electrode; etc.

One type of a secondary medical device includes an introducer, that may be used in a surgical procedure to move a primary medical device along an introduction axis, into or out of the patient. Secondary medical devices may also include a trajectory guide, or alignment device that positions the introducer in the direction of the area to be explored in the patient.

It is often desirable in precision surgical procedures such as neurosurgery that the exact position of the primary medical device is known in relation to the body of the patient. The relative position of the primary medical device is carefully controlled by secondary medical devices such as introducers and alignment devices. In one example, the alignment device fixes the introduction axis in three-dimensional space relative to the patient, and the introducer controls the position (depth inside the patient) of the primary medical device along the introduction axis.

To ensure that the secondary medical devices are accurately adjusted relative to the location of interest inside the patient, the alignment device is typically fixed relative to a patient reference frame. The patient reference frame includes the actual patient, and other objects or devices that the patient is fixed in relation to. The alignment device may therefore be fixed directly to the patient in one embodiment. Alternatively, the alignment device may be fixed to an intermediate object such as a stereotactic headframe or similar object attached to an operating table, with the patient being fixed to the operating table.

During positioning of an alignment device, an introduction axis is free to move in at least one degree of freedom, however after positioning is complete, it is desirable to have the introduction axis of the alignment device fixed in space. However, actuation of fixing devices typically causes an unwanted shift in the orientation of the introduction axis of the alignment device.

What is needed is a device and method to fix a desired position of an introduction axis of an alignment device with improved accuracy that reduces such unwanted shifting.

SUMMARY

The need for improved accuracy of alignment devices and fixing devices is addressed by the present invention and will be understood by reading and studying the following specification.

In one embodiment, an alignment device is described that includes a longitudinal guide portion, having a longitudinal opening. A guide axis is associated with the longitudinal opening. The alignment device also includes a deformable spherical portion coupled to an end of the longitudinal guide portion. The alignment device also includes a base unit, having a spherical socket for mating with the spherical portion. The alignment device also includes an actuating device coupled to the spherical socket. In one embodiment, the actuating device is not in direct contact with the spherical portion.

In one embodiment, an alignment device is described that includes a longitudinal guide portion, having a longitudinal opening. A guide axis is associated with the longitudinal opening. The alignment device also includes a spherical portion coupled to an end of the longitudinal guide portion. The alignment device also includes a base unit, having a spherical socket for mating with the spherical portion. The alignment device also includes at least one securing device adapted to secure the base unit to a working surface. There is at least one relief opening in a portion of the spherical socket, allowing deformation of the spherical socket. The alignment device also includes an actuating device coupled to the spherical socket. The actuating device is adapted to cause substantially symmetric tightening of the spherical socket around at least a part of the spherical portion. The alignment device also includes a number of standoff features attached to the base unit, wherein a substantial portion of the base unit is adapted to mount above the work surface.

In one embodiment, an alignment device is described that includes a longitudinal guide portion, having a longitudinal opening. A guide axis is associated with the longitudinal opening. The alignment device also includes a deformable spherical portion coupled to an end of the longitudinal guide portion. The alignment device also includes a base unit, having a spherical socket for mating with the spherical portion. The alignment device also includes an actuating device coupled to the spherical socket. In one embodiment, the actuating device is not in direct contact with the spherical portion. The alignment device also includes a number of standoff features attached to the base unit. The standoff features are adapted so that a substantial portion of the base unit can be mounted above the work surface. The alignment device also includes a screw retention feature coupled to the base unit.

In one embodiment, an alignment device is described that includes a longitudinal guide portion, having a longitudinal opening. A guide axis is associated with the longitudinal opening. The alignment device also includes an insert located substantially within the longitudinal opening wherein an outer diameter of the insert fits closely with the longitudinal opening, and an inner diameter is sized to fit closely with a device to be guided. The alignment device also includes a spherical portion coupled to an end of the longitudinal guide portion. The alignment device also includes a base unit, having a spherical socket for mating with the spherical portion. The alignment device also includes at least one securing device adapted to secure the base unit to a working surface. There is at least one relief opening in a portion of the spherical socket, allowing deformation of the spherical socket. There is at least one relief opening in a portion of the spherical socket, allowing deformation of the spherical socket. The alignment device also includes an actuating device coupled to the spherical socket. The actuating device is adapted to cause substantially symmetric tightening of the spherical socket around at least a part of the spherical portion. The alignment device also includes a number of standoff features attached to the base unit, wherein a substantial portion of the base unit is adapted to mount above the work surface.

In one embodiment, a method of manufacturing an alignment device is described. The method includes forming a longitudinal guide portion with a longitudinal opening that defines a guide axis. The method also includes attaching a spherical portion to an end of the longitudinal guide portion. The method also includes forming a base unit that includes a spherical socket for mating with the spherical portion, and opening a relief feature in a portion of the spherical socket to allow deformation of the socket. The method also includes coupling an actuating device to the spherical socket where the actuating device is adapted to cause substantially symmetric tightening of the spherical socket around at least a part of the spherical portion.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by the devices, procedures, combinations, etc. particularly pointed out in the appended claims.

DETAILED DESCRIPTION

Figure 1A:
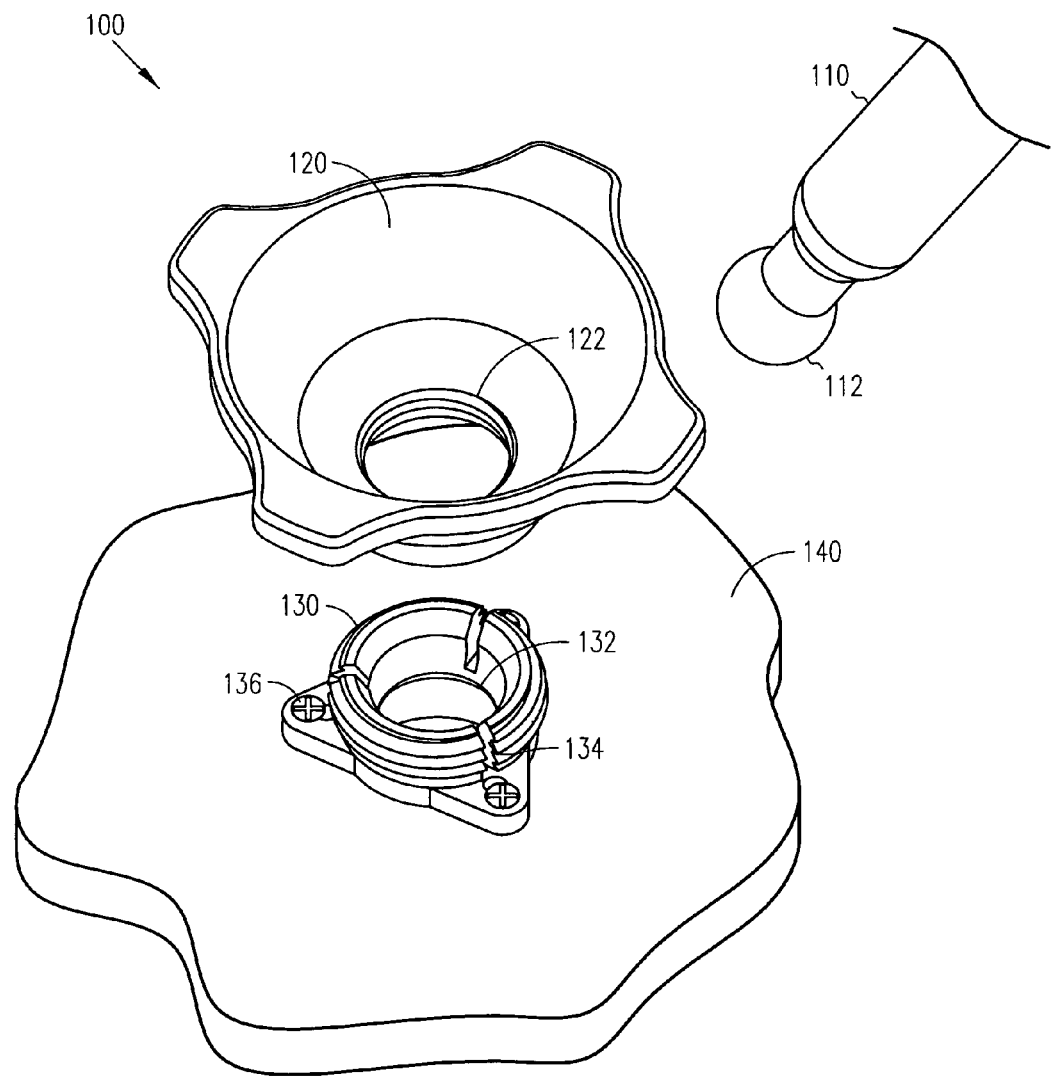
FIG. 1A shows an isometric and partially exploded view of an alignment device according to one embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical changes, etc. may be made without departing from the scope of the present invention.

In the following detailed description, directional terms such as "lateral" are defined in relation to a tangent plane with a work surface. In one example using a patient skull as a work surface, a lateral displacement is defined as within a plane that is tangent to an opening in the patient skull. Lateral displacement also includes a component of displacement that is within the tangent plane as described. Further, in the following detailed description the term spherical includes continuous spheres as well as portions of a sphere. For example, a hemisphere is defined to be included within the definition of a spherical portion.

FIG. 1A shows an alignment device 100 according to one embodiment of the invention. The alignment device 100 includes a longitudinal guide portion 110 that defines an introduction axis of the alignment device 100. A spherical portion 112 is shown located at a first end of the longitudinal guide portion 110.

The alignment device 100 also includes a base unit 130. The base unit 130 includes a spherical socket 132 that is adapted to mate with the spherical portion 112 of the longitudinal guide portion 110. A number of relief openings 134 are included in the spherical socket 132 that enhance and control deformation of the spherical socket 132. In one embodiment, three relief openings 134 are spaced around the spherical socket 132, although the invention is not so limited. One relief opening in the spherical socket 132, or other multiple numbers of relief openings 134 are also within the scope of the invention. In one embodiment, the number of relief openings 134 are symmetrically spaced, although the invention is not so limited.

A number of attaching devices 136 are also shown in FIG. 1A for attachment of the base unit 130 to a work surface 140. In one embodiment, the attaching devices 136 include bone screws. Other suitable attaching devices are also within the scope of the invention. In one embodiment, three bone screws are used, although other numbers of bone screws are also possible. In one embodiment, the work surface 140 includes patient tissue. In one embodiment, the work surface 140 includes a patient skull for a neurosurgical procedure. In one embodiment, the base unit 130 is attached to an intermediate structure such as a stereotactic headframe, which is in turn fixed to a patient skull. Although surgical embodiments of the base unit are discussed in the present description, the invention may be used in other alignment procedures apart from medical applications.

An actuating device 120 is further shown in FIG. 1A. The actuating device 120 is designed such that when actuated, the spherical socket 132 is tightened about the spherical portion 112 of the longitudinal guide portion 110 in a substantially symmetric manner. In the present description, a definition of symmetric includes uniform motion of clamping surfaces. This is in contrast to one clamping surface being fixed with an opposing clamping surface moving towards the fixed surface. Using the embodiment of the alignment device 100 as an example, symmetric clamping is accomplished when multiple portions of the spherical socket 132 move at the same time during actuation of the actuating device. Using symmetric clamping, the spherical portion 112 is not substantially displaced in relation to the subject during clamping. Instead, the spherical socket 132 deforms to clamp symmetrically around the spherical portion 112, thus reducing unwanted lateral motion of the spherical portion 112. In one embodiment, symmetric clamping is facilitated with lateral deformation of portions of the spherical socket 132. Although substantially lateral deformation is shown, the invention is not so limited. Symmetric deformation along other orientations of the spherical socket 132 is also within the scope of the invention.

In one embodiment as shown in FIG. 1A, the actuating device 120 includes a threaded portion that mates with corresponding threads on the base unit 130. The threads on the base unit 130 are located around a periphery of the spherical socket 132. In one embodiment, the threads on the actuating device 120 include a deflecting ridge 122 that causes tightening of the spherical socket 132 when the actuating device 120 is threaded onto the base unit 130. In one embodiment, the threads on the base unit are tapered to facilitate tightening of the spherical socket 132 as the actuating device 120 is threaded down onto the base unit 130.

Although a threaded embodiment of an actuating device 120 is shown, other embodiments of actuating devices are included within the scope of the invention. For example, an alternative actuating device may include a band that is tightened about the spherical socket 132 using a device such as a cam lever.

Figure 1B:
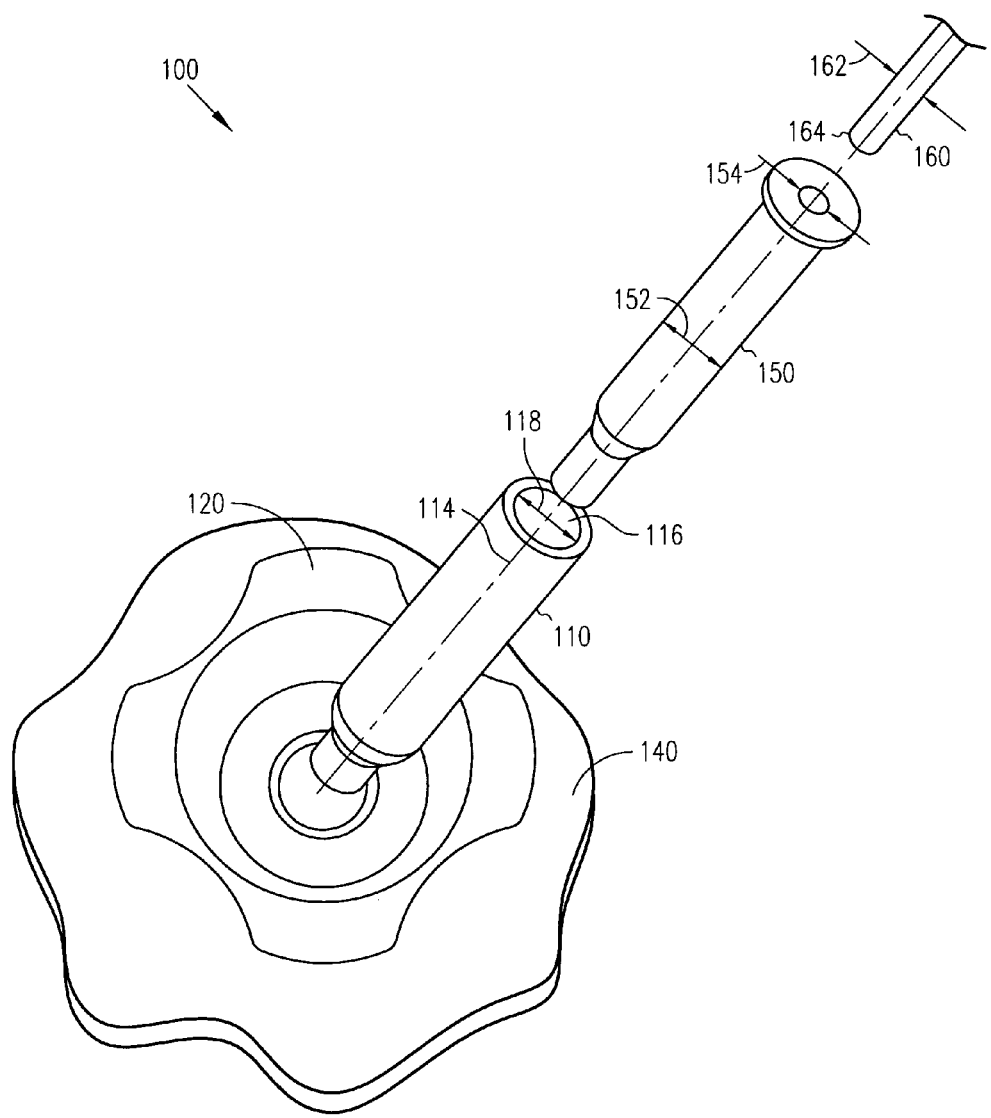
FIG. 1B shows another isometric and partially exploded view of an alignment device according to one embodiment of the invention.

FIG. 1B shows the longitudinal guide portion 110 with the spherical portion 112 in place within the spherical socket 132 of the base unit 130. The actuating device 120 is shown in an actuated state that fixes an orientation of the insertion axis. The insertion axis is illustrated in FIG. 1B as element 114.

In one embodiment, the longitudinal guide portion 110 includes a bore opening 116 with a diameter 118. A primary medical device 160 is further shown with a diameter 162. As discussed above, several varieties of primary medical device are possible. In one embodiment, the primary medical device 160 includes a catheter structure with an active distal end 164 that includes, but is not limited to: a biopsy probe; drug delivery capability; a tissue removal instrument such as a laser; an instrument for placing an electrode; etc.

In one embodiment, the diameter 118 is larger than the diameter 162 of the primary medical device 160. An insert 150 is included in one embodiment. The insert 150 includes an outer diameter 152 that is sized to fit closely with the diameter 118 of the bore 116. The insert 150 further includes an inner diameter 154 that is sized to fit closely with the diameter 162 of the primary medical device 160. In embodiments utilizing an insert 150, a single alignment device 100 can be used with several different primary medical devices 160, each having a different diameter 162. The user need only have a corresponding insert 150 to match the diameter 162 of the primary device 160 with the diameter 118 of the bore 116.

Figure 1C:
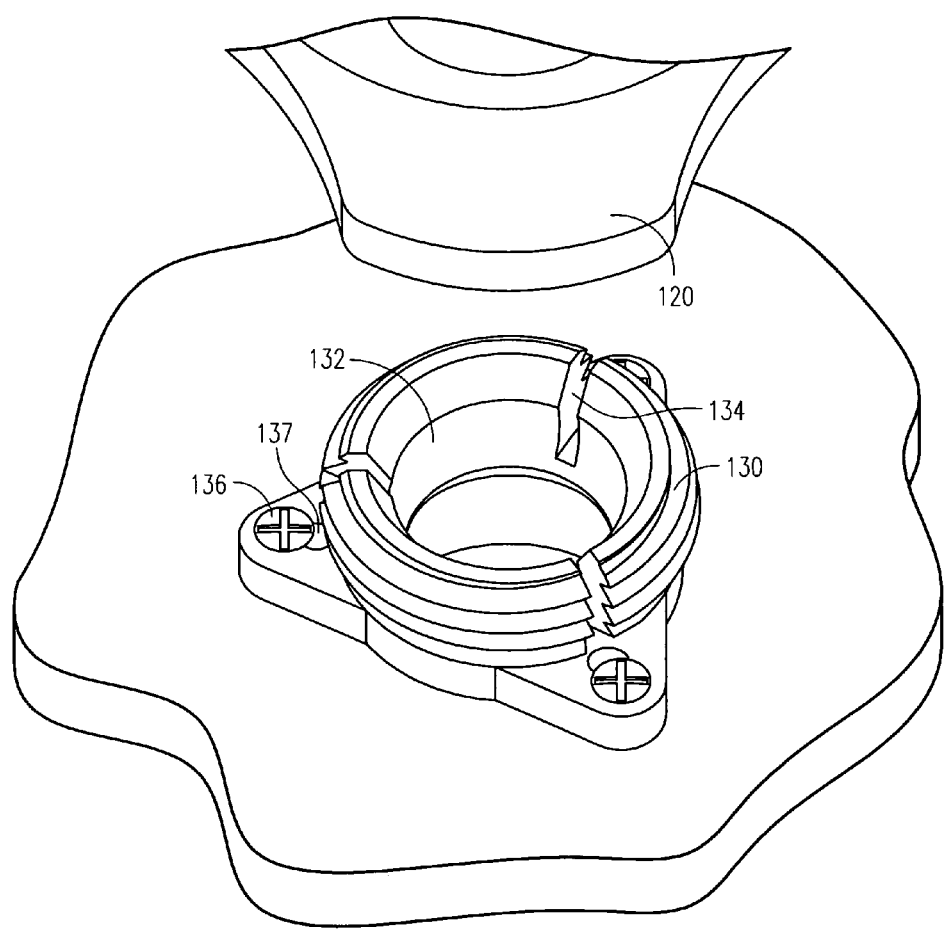
FIG. 1C shows an isometric view of selected components of an alignment device according to one embodiment of the invention.

FIG. 1C shows a closer view of the base unit 130 with a portion of the actuating device 120 shown above the base unit 130. An insert material 137 is shown adjacent to, and in contact with a portion of the attachment device 136. The insert material 137 is deformable, and provides an interference fit with the attaching device such as a bone screw 136. In one embodiment, the insert material 137 includes a silicone material. In one embodiment, the insert material 137 is configured to deform and provide a retention force against the attaching device such as a bone screw 136. However, the retention force provided by the insert material 137 does not inhibit actuation of the attaching device 136. In this way, attaching devices are held in place on the base unit 130, ready for attachment such as screwing into a patient. The attachment devices 136 are therefore not easily dropped on the floor, and the base unit 130 can be attached to a patient more easily. In one method, the base unit 130 can be attached to a patient using one hand to hold the base unit, and one hand to hold a screwdriver.

When the spherical portion 112 of the longitudinal guide portion 110 is inserted into the spherical socket 132 of the base unit 130, a large range of orientations of the longitudinal guide portion 110 and corresponding insertion axis 114 are possible. The longitudinal guide portion 110 rotates in multiple degrees of rotational freedom about the center of the spherical portion 112 within the spherical socket 132. The ability to adjust multiple degrees of rotational freedom at the same time is desirable, and speeds up the process of aligning the insertion axis during a procedure.

Once a desired orientation of the insertion axis 114 is achieved, it is desirable to fix the insertion axis 114 in three dimensional space, thus determining a trajectory for insertion of the primary medical device 160. Once the orientation of the insertion axis 114 is achieved, the actuating device 120 is actuated to fix the insertion axis orientation. In one embodiment, the number of relief openings 134 allow the spherical socket 132 to symmetrically deform during actuation of the actuating device 120. The symmetric deformation of the spherical socket 132 clamps on the spherical portion 112 to symmetrically fix rotation of the spherical portion 112 within the base unit 130. Symmetrical clamping reduces or eliminates any lateral motion of the spherical portion 112 relative to the base unit during actuation of the actuating device. In contrast, actuation devices that do not clamp symmetrically, for example a set screw pushing from only one side of a socket joint, cause unwanted lateral displacement of the spherical portion 112, and thus the insertion axis 114.

Further, embodiments using a deformable socket such as the spherical socket 132 do not impart other unwanted forces that have a bearing on the alignment axis. For example, no torque forces are imparted on the spherical portion 112 during actuation of the actuating device 120. Because the spherical socket 132 does not rotate during clamping, and because the actuating device 120 does not contact the spherical portion 112, no torque forces are transmitted, thus improving the alignment accuracy of embodiments of alignment devices shown.

Figure 2:
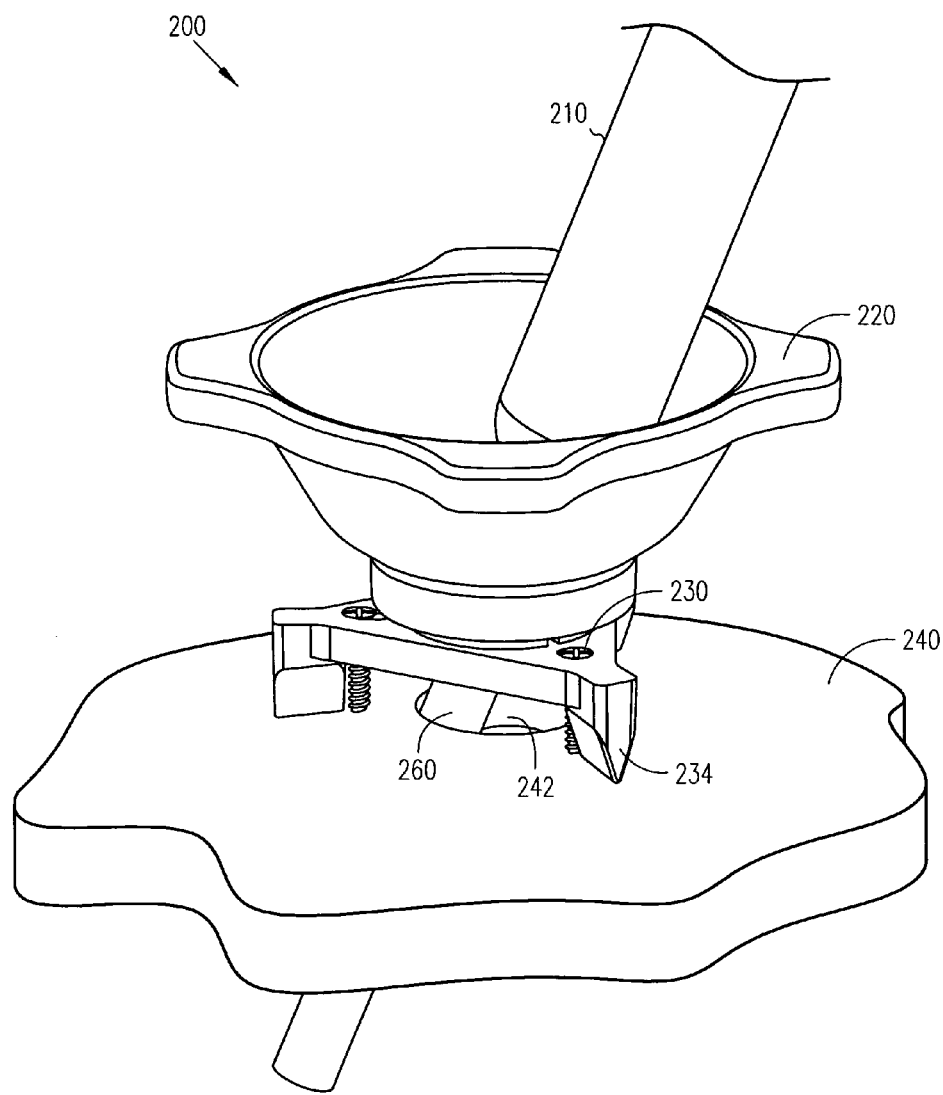
FIG. 2 shows an isometric view of an alignment device according to one embodiment of the invention.

FIG. 2 shows an embodiment of an alignment device 200. The alignment device 200 includes a longitudinal guide portion 210 that defines an introduction axis of the alignment device 200. A spherical portion is included at a first end of the longitudinal guide portion 210 similar to embodiments described above. A primary medical device 260 is shown passing along an insertion axis through an opening 242 in the work surface 240, such as a burr hole in a patient skull.

The alignment device 200 also includes a base unit 230. The base unit 230 includes a spherical socket similar to embodiments described above that is adapted to mate with the spherical portion of the longitudinal guide portion 210. A number of relief openings are further included in the embodiment shown in FIG. 2, although they are not visible in the Figure. Similar to embodiments described above, actuation of an actuating device 220 provides symmetric clamping of the spherical portion of the longitudinal guide portion 210. The symmetric clamping significantly reduces any unwanted lateral displacement of the longitudinal guide portion 210 and corresponding insertion axis during actuation of the actuating device 220.

In one embodiment, the base unit 230 further includes a number of standoff features 234. The standoff features 234 shown in FIG. 2 include a substantially linear contact surface. In one embodiment, the standoff features 234, as well as the substantially linear contact surface, help to reduce tissue damage due to attachment of the insertion guide device to a subject. The standoff features 234 further allow a user to perform certain procedures underneath the base unit 230 and adjacent to the opening 242.

In surgical procedures where a device is attached directly to a surface of a patient, tissue damage is an issue. In one embodiment, tissue damage is reduced by contacting the patient surface at a minimum number of locations and/or using a reduced contact area. In one embodiment, three standoff features 234 are used to maintain a stable platform for the alignment device 200 while minimizing a number of contact locations and/or reducing the contact area. In one embodiment, the standoff features 234 are located apart from the opening in the subject, such as a burr hole. The remote location of standoff features 234 reduces tissue damage at the opening or burr hole location. In use, the standoff features 234 raise a substantial portion of the alignment device 200 above the subject surface 240. By raising the alignment device 200 above the subject surface, tissue damage due to pinching large amounts of tissue under the alignment device 200 is avoided.

A substantially linear contact surface of the standoff features 234 is desirable for procedures that use a linear cutting instrument to pierce tissue on a subject's scalp prior to attachment. In one embodiment, a scalpel is used to pierce the scalp along a linear incision, thus making a substantially linear contact surface of the standoff features 234 convenient.

One example of a procedure that is useful and can performed underneath the base unit 230 and adjacent to the opening 242 includes holding a primary medical device 260 with forceps. If a primary medical device 260 is to remain in a patient for an extended period of time it is useful to be able to hold the primary medical device 260 in place while removing other devices such as the base unit 230. In one embodiment elements of an alignment device 200 such as the base unit 230 are formed from transparent materials such as polycarbonate to further enable a user to visualize procedures underneath the base unit 230.

Figure 3A:
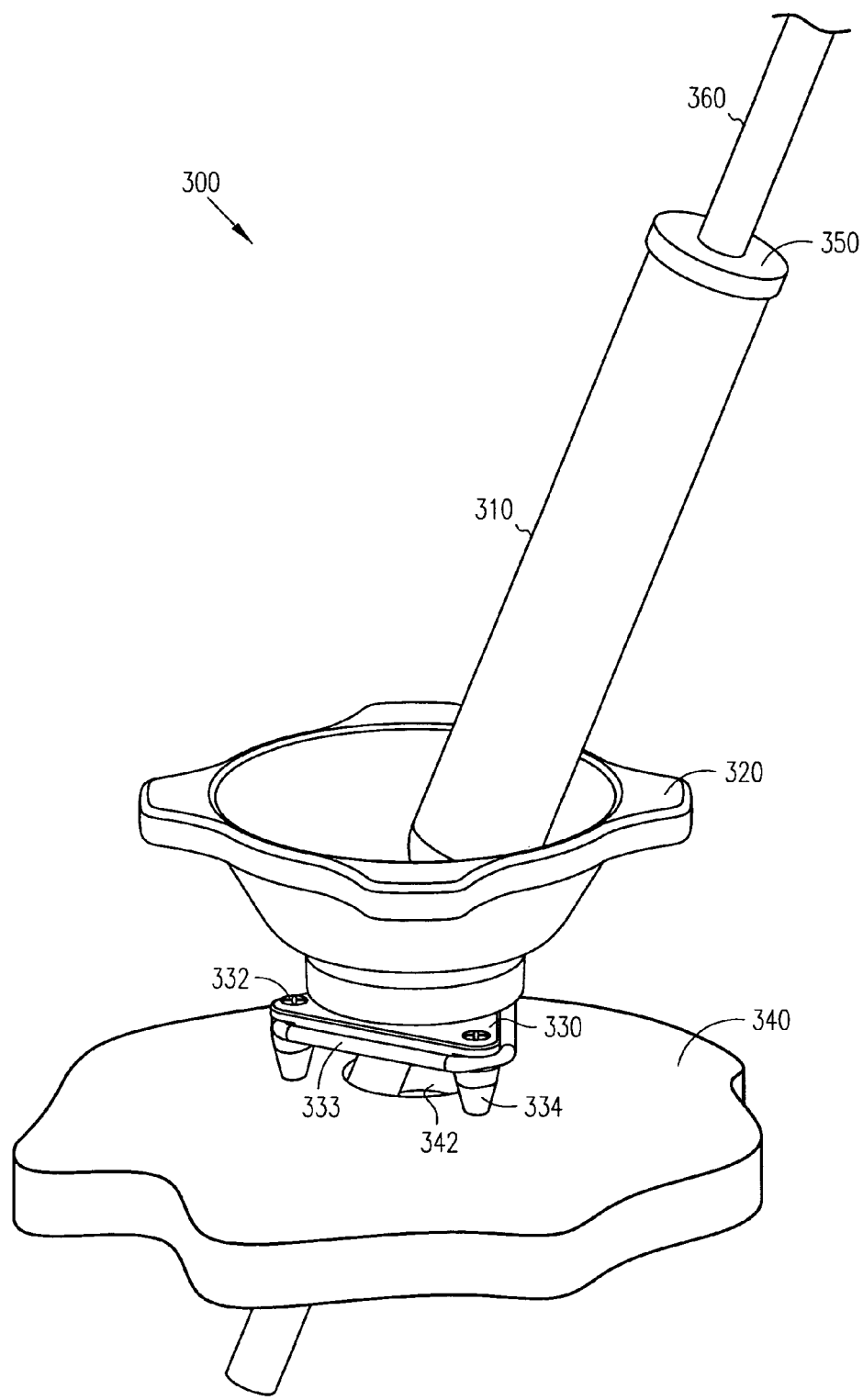
FIG. 3A shows an isometric view of another alignment device according to one embodiment of the invention.

FIG. 3A shows an embodiment of an alignment device 300. The alignment device 300 includes a longitudinal guide portion 310 that defines an introduction axis of the alignment device 300. A spherical portion is included at a first end of the longitudinal guide portion 310 similar to embodiments described above. A primary medical device 360 is shown passing through an insert 350 through an opening in the work surface 340, such as a burr hole 342 in a patient skull.

The alignment device 300 also includes a base unit 330. The base unit 330 includes a spherical socket similar to embodiments described above that is adapted to mate with the spherical portion of the longitudinal guide portion 310. A number of relief openings are further included in the embodiment shown in FIG. 3A, although they are not visible in the Figure. Similar to embodiments described above, actuation of an actuating device 320 provides symmetric clamping of the spherical portion of the longitudinal guide portion 310. The symmetric clamping significantly reduces any unwanted lateral displacement of the longitudinal guide portion 310 and corresponding insertion axis during actuation of the actuating device 320.

In one embodiment, the base unit 330 further includes a number of standoff features 334. The standoff features 334 shown in FIG. 3A include a substantially circular contact surface. In one embodiment, the standoff features 334, as well as the substantially circular contact surface, help to reduce tissue damage due to attachment of the insertion guide device to a subject.

In one embodiment a truncated cone shape of the standoff features 334 reduces a contact surface to a reduced area, while sufficient support for an attaching device 332 such as a bone screw is provided. A substantially circular contact surface of the truncated cone standoff features 334 is desirable for procedures that use a circular cutting instrument to pierce tissue on a subject's scalp prior to attachment. In one embodiment, a hypodermic needle is used to pierce the scalp in a circular incision, thus making a substantially circular contact surface of the standoff features 334 convenient.

Figure 3B:
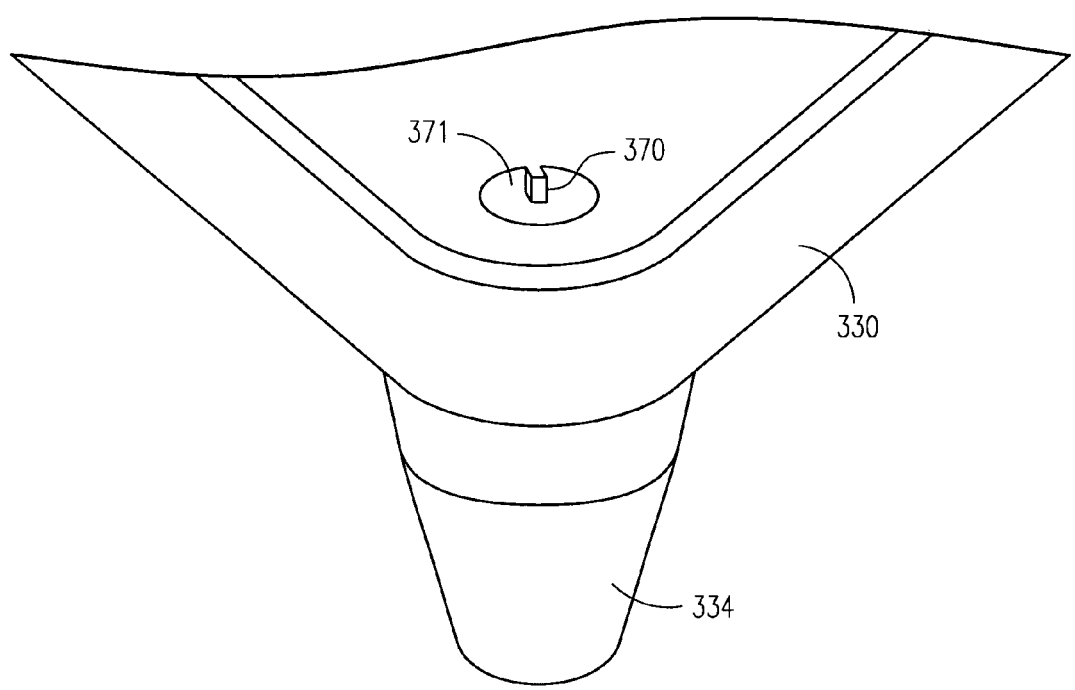
FIG. 3B shows an isometric view of a standoff feature according to one embodiment of the invention.

In one embodiment, an elastomeric portion 333, such as an elastomeric band is included to provide a retention force for the attaching devices 332 such as bone screws. As illustrated in FIGS. 3A and 3B, the base unit 330 defines a groove at a perimeter of the base unit 330. The groove is operable to hold the elastomeric portion 333 such that a portion of an elastomeric portion 333 extends into a passage of the standoff features 334.

However, the retention force provided by the elastomeric portion 333 does not inhibit actuation of the attaching devices 332. In this way, attaching devices 332 are held in place on the base unit 330, ready for attachment such as screwing into a patient. The attachment devices are therefore not easily dropped on the floor, and the base unit 330 can be attached to a patient more easily. In one method, the base unit 330 can be attached to a patient using one hand to hold the base unit, and one hand to hold a screwdriver.

FIG. 3B shows an embodiment of the base unit 330. The base unit 330 further includes a number of standoff features 334. An opening 371 is shown within the standoff feature 334 to accept an attaching device such as a bone screw (not shown). The standoff feature 334 shown in FIG. 3B includes a substantially circular contact surface as described in embodiments above. The truncated cone shape of the standoff feature 334 shown in FIG. 3B reduces a contact surface area, while providing sufficient support for the attaching device such as a bone screw.

FIG. 3B further includes a protruding structure 370, extending into the opening 371. The protruding structure 370 is deformable, and provides an interference fit with the attaching device such as a bone screw. In one embodiment, the protruding structure 370 is configured to deform and provide a retention force against the attaching device such as a bone screw. However, the retention force provided by the protruding structure 370 does not inhibit actuation of the attaching device. In this way, attaching devices are held in place on the base unit 330, ready for attachment such as screwing into a patient. The attachment devices are therefore not easily dropped on the floor, and the base unit 330 can be attached to a patient more easily. In one method, the base unit 330 can be attached to a patient using one hand to hold the base unit, and one hand to hold a screwdriver.

In one embodiment, the protruding structure 370 is integrally formed with the base unit 330. In one embodiment, the base unit 330 and the protruding structure 370 are integrally formed from a polymer, such as polycarbonate.

Figure 3C:
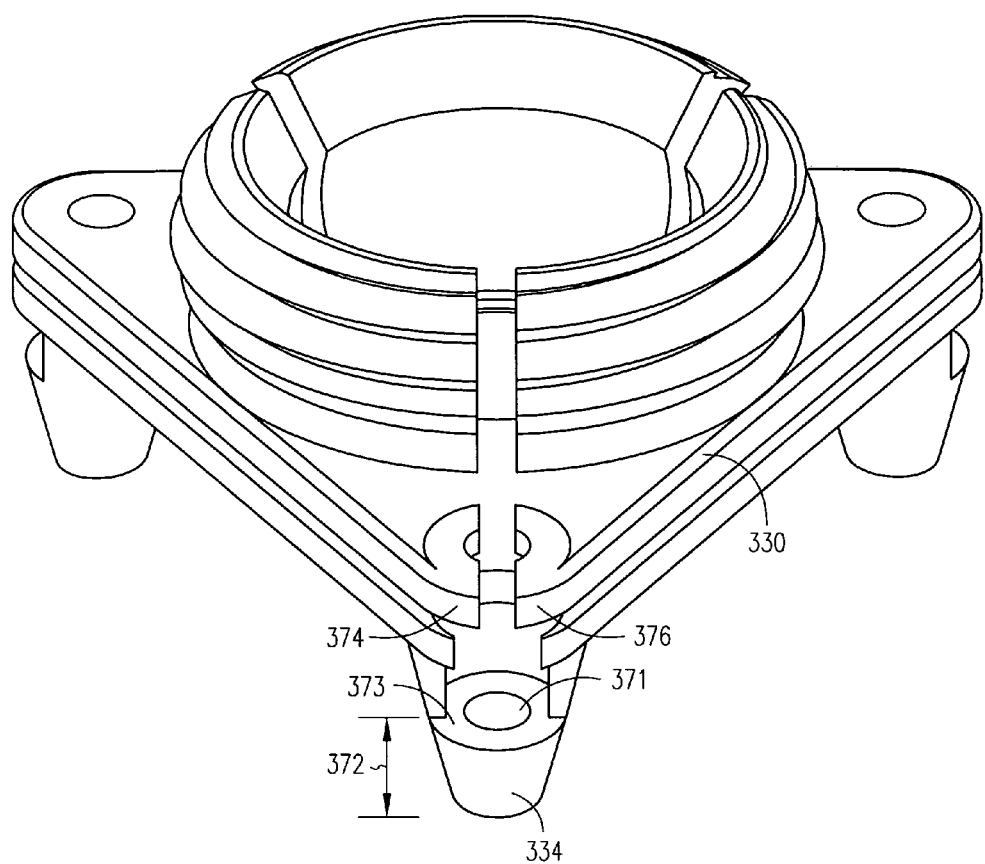
FIG. 3C shows an isometric view of another standoff feature according to one embodiment of the invention.

FIG. 3C shows an embodiment of the base unit 330. The base unit 330 further includes a number of standoff features 334. An opening 371 is shown within the standoff feature 334 to accept an attaching device such as a bone screw (not shown). The standoff feature 334 includes a shelf 373 that determines an attachment thickness 372. When attachment devices such as bone screws are used, they will tighten against the shelf 373 to secure the base unit 330 to the patient surface.

In one embodiment, the shelf 373 of the standoff feature 334 is positioned so that the attachment thickness 372 is substantially the same as other common devices using similar attachment devices. For example, bone screws designs are available for use with other neurosurgical devices. The existing bone screw designs have a length that is appropriate for current attachment thicknesses of other devices. In one embodiment the attachment thickness 372 is configured to utilize existing bone screw lengths. In one embodiment, the attachment thickness 372 is configured for compatibility with attachment devices such as bone screws that are also compatible with a thickness of the base unit 130 from FIG. 1C.

FIG. 3C also shows a first feature 374 and a second feature 376 that are located adjacent to an axis of the opening 371. In one embodiment the first feature 374 and the second feature 376 are configured to deform and provide a retention force against the attaching device such as a bone screw. However, the retention force provided by the first feature 374 and the second feature 376 does not inhibit actuation of the attaching device. In this way, attaching devices are held in place on the base unit 330, ready for attachment such as screwing into a patient. The attachment devices are therefore not easily dropped on the floor, and the base unit 330 can be attached to a patient more easily. In one method, the base unit 330 can be attached to a patient using one hand to hold the base unit, and one hand to hold a screwdriver.

Figure 4:
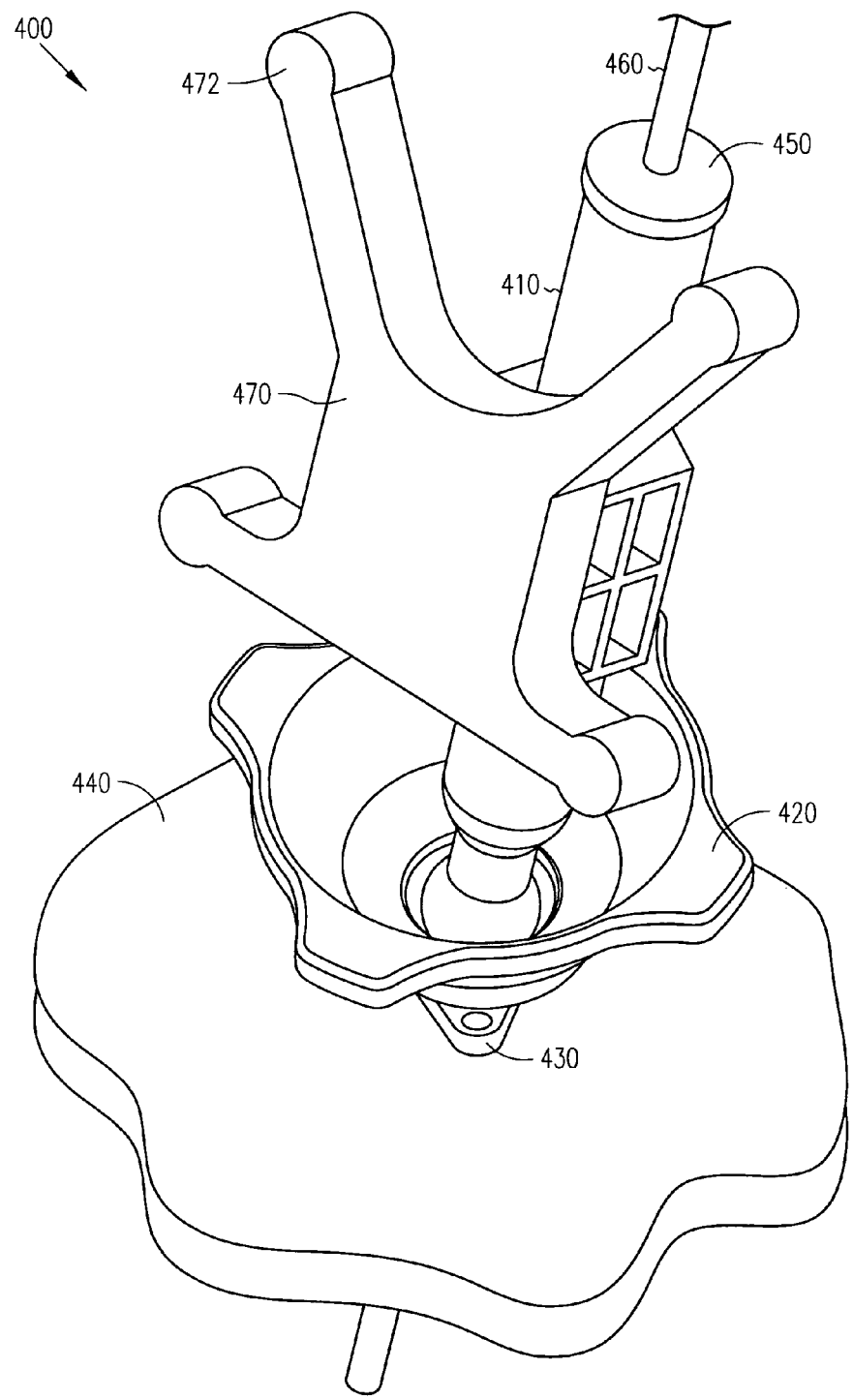
FIG. 4 shows an isometric view of an assembly including an alignment device according to one embodiment of the invention.

FIG. 4 shows an alignment device 400 according to an embodiment of the invention. The alignment device 400 includes a longitudinal guide portion 410 that defines an introduction axis of the alignment device 400. A spherical portion is included at a first end of the longitudinal guide portion 410 similar to embodiments described above. A primary medical device 460 is shown passing through an insert 450 that is positioned at least partially within the longitudinal guide portion 410.

The alignment device 400 also includes a base unit 430, shown attached to a patient work surface 440. The base unit 430 includes a spherical socket similar to embodiments described above that is adapted to mate with the spherical portion of the longitudinal guide portion 410. A number of relief openings are further included in the spherical socket of the base unit 430, although they are not visible in the Figure. Similar to embodiments described above, actuation of an actuating device 420 provides symmetric clamping of the spherical portion of the longitudinal guide portion 410. The symmetric clamping helps to significantly reduce any unwanted lateral displacement of the longitudinal guide portion 410 and corresponding insertion axis during actuation of the actuating device 420.

In one embodiment, an orienting fixture 470 is attached to the longitudinal guide portion 410. In one embodiment, the orienting fixture 470 is detectable using at least one imaging method. In one embodiment, an imaging method includes remote positioning systems using infra red (IR) light detection. In one embodiment, detection is facilitated using a number of detectable points 472, such as reflective structures or light emitting diodes (LED's) included on the orienting fixture 470. One suitable orienting fixture 470 includes the StealthFighter™, manufactured by Medtronic Inc. of Minneapolis, Minn.

In one embodiment, an imaging method includes a tissue imaging method. Suitable tissue imaging methods include, but are not limited to: magnetic resonance imaging (MRI); computed tomography (CT); ultrasound imaging; etc. The orienting fixture 470 is used in one embodiment to provide real time imaging of the insertion axis concurrent to imaging of tissue. This allows a user to adjust the aligning device 400 to target a location within a patient in real time.

Figure 5:
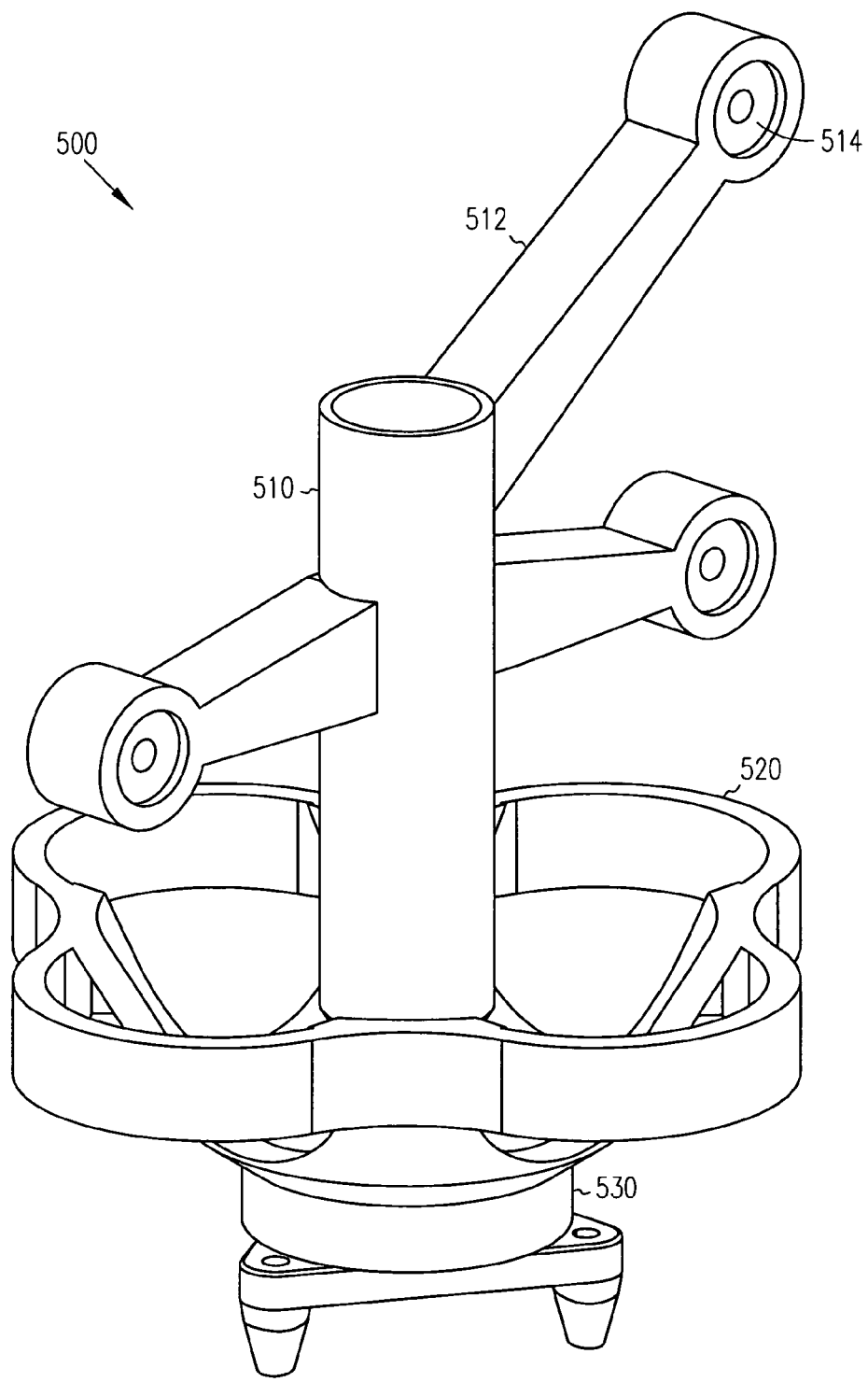
FIG. 5 shows an isometric view of another assembly including an alignment device according to one embodiment of the invention.

FIG. 5 shows an alignment device 500 according to an embodiment of the invention. The alignment device 500 includes a longitudinal guide portion 510 that defines an introduction axis of the alignment device 500. A spherical portion is included at a first end of the longitudinal guide portion 510 similar to embodiments described above.

The alignment device 500 also includes a base unit 530. The base unit 530 includes a spherical socket similar to embodiments described above that is adapted to mate with the spherical portion of the longitudinal guide portion 510. A number of relief openings are further included in the spherical socket of the base unit 530, although they are not visible in the Figure. Similar to embodiments described above, actuation of an actuating device 520 provides symmetric clamping of the spherical portion of the longitudinal guide portion 510. In one embodiment, the actuating device 520 further does not directly contact the spherical portion of the longitudinal guide portion 510 thus removing rotational displacement during actuation of the actuating device 520.

In one embodiment, a number of extending members 512 are attached to the longitudinal guide portion 510. In one embodiment, the number of extending members 512 are integrally formed with the longitudinal guide portion 510. a number of detection devices 514 are located on the number of extending members 512. Similar to the embodiment of FIG. 4, the number of detection devices 514 are detectable using any of several detection and imaging methods. In one embodiment, three extending members 512 and three detection devices 514 are integrally molded with the longitudinal guide portion 510. The use of integral molding and three extending members 512 further reduces the manufacturing cost of the alignment device 500. One desirable embodiment of an alignment device is inexpensive to manufacture and can be used as a disposable, one time use device.

Figure 6:
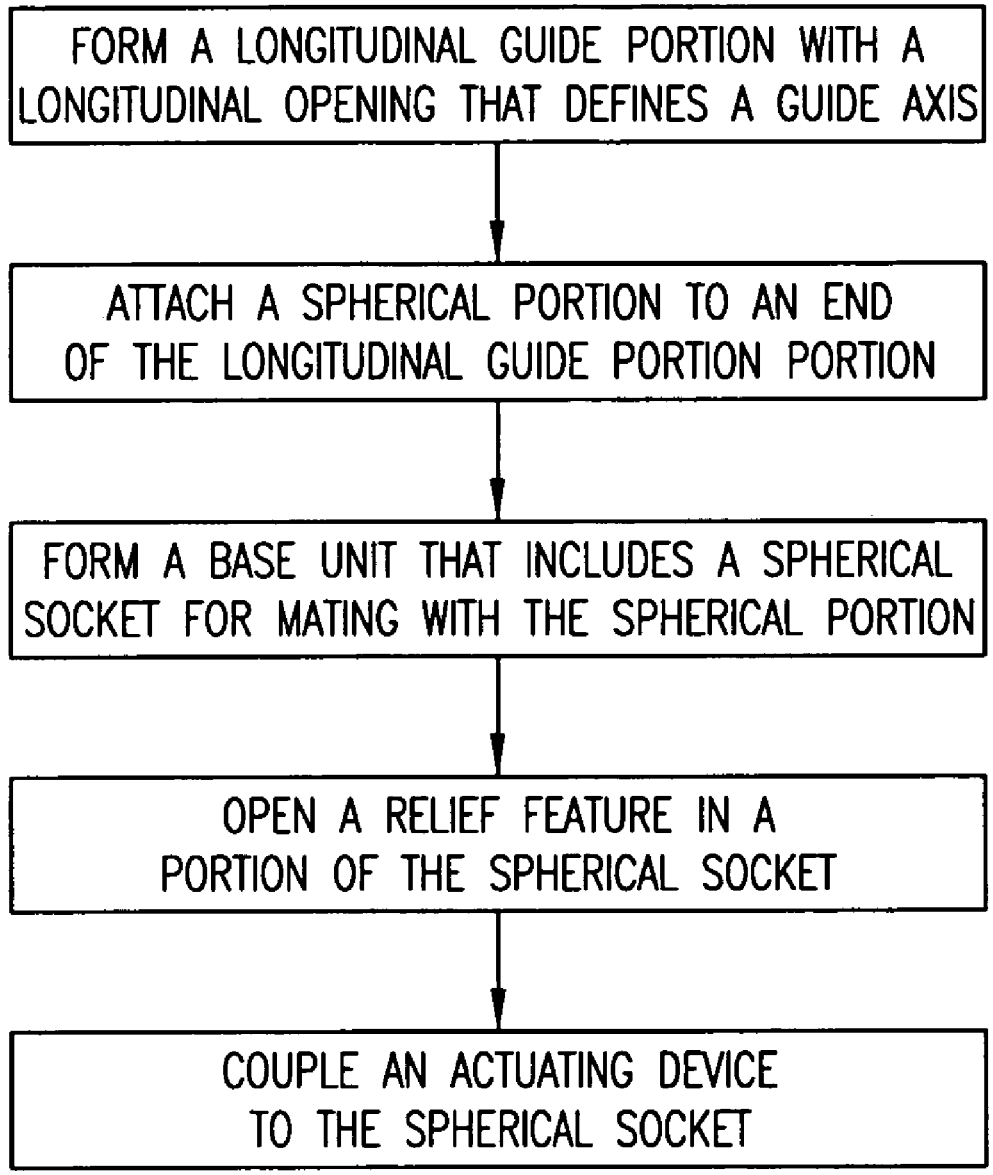
FIG. 6 shows a flow diagram for an alignment device according to one embodiment of the invention.

FIG. 6 shows a flow diagram of one possible manufacturing method. A longitudinal guide portion is formed with a longitudinal opening that defines a guide axis. A spherical portion is attached to an end of the longitudinal guide portion. A base unit is formed that includes a spherical socket for mating with the spherical portion. A relief feature is opened in a portion of the spherical socket, allowing deformation of the socket. An actuating device is coupled to the spherical socket. The actuating device is manufactured and attached in such a way, that when it is actuated, it causes substantially symmetric tightening of the spherical socket around at least a part of the spherical portion.

CONCLUSION

Using embodiments described above, a number of advantages are realized. Embodiments of alignment devices are described that provide higher precision when fixing an orientation of an insertion axis. Features of embodiments shown include, but are not limited to: a symmetric clamping force; a deformable socket portion; uniform clamping; and lateral clamping. Further, selected embodiments shown above include an actuation device that is not in direct contact with any part of the longitudinal guide portion. These features, among others, reduce or eliminate unwanted displacement such as lateral or rotational displacement of the insertion axis after the desired orientation is obtained.

Selected embodiments include an insert that allows several varieties of primary medical devices to be used with a single alignment device. The use of an insert therefore increases flexibility for the end user and increases manufacturing efficiency.

Selected embodiments include a number of standoff features that reduce tissue damage to a patient when direct mounting is used. The standoff features utilize a reduced contact surface with the patient so that less tissue is contacted by the device. Further, the standoff features leave more room around the opening in the patient which increases visibility for the surgeon and allows access to the opening.

Selected embodiments further include an orienting fixture that moves in relation to the insertion axis of an alignment device. The addition of an orienting fixture permits a user to view the insertion axis in real time using image guided techniques and software.

Although selected advantages are detailed above, the list is not intended to be exhaustive. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. An alignment device, comprising:
   a longitudinal guide portion, having a longitudinal opening including a guide axis;
   a spherical portion coupled to an end of the longitudinal guide portion;
   a base unit, including:
   a deformable substantially spherical socket formed of a socket member engaging the spherical portion including at least one relief opening in a portion of the spherical socket allowing deformation of the spherical socket; and a substantially planar portion wherein the socket member of the spherical socket extends from a first side of the substantially planar portion; and
   an actuating device surrounding and engaging an outer perimeter of the spherical socket, wherein the actuating device is not in direct contact with the spherical portion; and
   a number of standoff features attached to the base unit, wherein the standoff features are adapted to directly contact a skull of a subject adjacent to an opening in the skull, wherein the number of standoff features attached to the base unit extend from a second side of the substantially planar portion away from the socket member to position the substantially planar portion a distance away from the skull.

2. The alignment device of claim 1, wherein the actuating device is adapted to cause substantially symmetric tightening of the spherical socket around at least a part of the spherical portion.

3. The alignment device of claim 1, wherein the actuating device includes a threaded locking ring adapted to engage a number of threads coupled to the spherical socket.

4. The alignment device of claim 1, wherein the at least one relief opening includes three relief openings substantially equally spaced about a circumference of the spherical socket;
   wherein the socket member includes a plurality of socket members; wherein one relief opening is between each of the plurality of socket members.

5. The alignment device of claim 4, wherein the relief openings are defined as a complete passage between at least two of the plurality of socket members defining at least a portion of the spherical socket of the base.

6. The alignment device of claim 1, wherein at least one standoff feature is adapted to contact the work surface along a line.

7. The alignment device of claim 1, wherein at least one standoff feature is adapted to contact the work surface along a circle.

8. The alignment device of claim 1, further including an orienting fixture attached to the longitudinal guide portion, wherein the orienting fixture is detectable using tissue imaging techniques.

9. The alignment device of claim 1, wherein at least one standoff feature includes a shelf to determine an attachment thickness in combination with a bone screw wherein the attachment thickness is less than a standoff feature thickness.

10. The alignment device of claim 1, wherein the substantially spherical socket defines less than an entire sphere.

11. The alignment device of claim 1, wherein the actuating device engages an entire perimeter of the spherical socket.

12. The alignment device of claim 1, further including:
    a shelf that extends into a bore defined by each of the number of standoff features;
    wherein each of the number of standoff features extend from a first standoff feature end at the substantially planar portion to a second standoff feature end;
    wherein the shelf defines a surface intermediate the first standoff feature end and the second standoff feature end.

13. The alignment device of claim 1,
    wherein the deformable substantially spherical socket is operable to allow the guide axis to be positioned in at least two angles relative to the base unit.

14. An alignment device, comprising:
    a longitudinal guide portion, having a longitudinal opening including a guide axis;
    a spherical portion coupled to an end of the longitudinal guide portion;
    a base unit, having a spherical socket for engaging with the spherical portion and a substantially planar portion wherein the spherical socket extends from a first side of the substantially planar portion wherein the spherical socket includes at least two members deformably connected to the first side of the substantially planar portion;
    a number of securing devices adapted to secure the base unit to a skull;
    at least two relief openings in a portion of the spherical socket defined by a complete disassociation of at least two portions of the spherical socket, allowing deformation of the spherical socket, wherein the relief openings includes the complete disassociation of the at least two portions from each other above the substantially planar portion to allow each of the at least two portions to bend from the planar portion;
    an actuating device coupled to the spherical socket to cause substantially symmetric tightening of the spherical socket around at least a part of the spherical portion; and
    a number of standoff features attached to the base unit that extend from a second side of the substantially planar portion such that the standoff members extend in a direction substantially away from the spherical socket;
    wherein the number of standoff features are adapted for placement adjacent to an opening in a skull of a subject, and
    wherein the substantially planar portion of the base unit and the spherical socket is adapted to mount a distance away from the skull where the standoff features contact the skull.

15. The alignment device of claim 14, wherein the number of standoff features attached to the base unit includes three standoff features.

16. The alignment device of claim 14, wherein the number of standoff features attached to the base unit includes a truncated cone shaped standoff feature.

17. The alignment device of claim 16, where at least one of the securing devices extends a length of the truncated cone to engage the skull.

18. The alignment device of claim 14, wherein the actuating device includes a threaded locking ring adapted to engage a number of threads coupled to the spherical socket.

19. The alignment device of claim 14, wherein the at least two relief openings include three relief openings substantially equally spaced about a circumference of the spherical socket.

20. The alignment device of claim 14, wherein the securing devices pass through at least a portion of the standoff features.

21. The alignment device of claim 14, further including:
a shelf that extends into a bore defined by each of the number of standoff features;
wherein each of the number of standoff features extend from a first standoff feature end at the substantially planar portion to a second standoff feature end;
wherein the shelf defines a surface intermediate the first standoff feature end and the second standoff feature end;
wherein a portion of the substantially planar portion extends over the bore at the first standoff feature end.

22. An alignment device, comprising:
a longitudinal guide portion, having a longitudinal opening including a guide axis;
a spherical portion coupled to an end of the longitudinal guide portion;
a base unit operable to be positioned relative to a work surface, having a deformable spherical socket mating with the spherical portion; and
an actuating device operatively connected to the spherical socket, wherein the actuating device is not in direct contact with the spherical portion;
at least two standoff features each having a standoff feature thickness attached to the base unit, wherein a substantial portion of the base unit is adapted to mount above the work surface, wherein each of the at least two standoff features define a passage through which an attaching device is operable to pass substantially freely and engage the work surface to fix the base unit to the work surface; and
a retention force providing member coupled to the base unit and operable to retain the attaching device near the passage;
wherein the guide axis extends through the base unit and between the at least two standoff features;
wherein the retention force providing member is an elastomeric band;
wherein the base defines a groove at a perimeter of the base operable to hold the elastomeric band.

23. An alignment device, comprising:
a longitudinal guide portion, having a longitudinal opening including a guide axis;
a spherical portion operably coupled to an end of the longitudinal guide portion;
a base unit, including:
a first portion having a first side and a second side and an outer perimeter, wherein the first portion defines a passage extending from the first side through the second side within the outer perimeter;
a single deformable substantially spherical socket including at least two individual members attached to and extending separately and away from the first side of the outer perimeter of the first portion for mating with the spherical portion, wherein a relief opening is defined as a complete separation between the at least two individual members extending from an outer surface of each of the individual members to an inner surface of each of the individual members and the at least two individual members are operable to deform relative to the first portion independently of one another;
an actuating device that surrounds and engages all of the individual members of the spherical socket to substantially symmetrically compress the at least two individual members of the substantially spherical socket, wherein the actuating device is not in direct contact with the spherical portion;
a plurality of standoff feature extending from the base unit, wherein the standoff features are is adapted to directly engage a work surface near an opening in the work surface;
a passage defined through each of the standoff features;
an attaching device operable to pass through each passage and engage the work surface; and
a retaining force applying member operable to hold the attaching device relative to the passage at least prior to moving the attaching device relative to the work surface.

24. The alignment device of claim 23, wherein the work surface is a skull of a subject.

25. The alignment device of claim 23, wherein the outer perimeter of the spherical socket includes an external thread and the actuating device defines an internal thread operable to engage the external thread;
wherein the actuating member is operable to move relative to the spherical socket, via interaction with the internal thread;
wherein as the actuating member moves relative to the spherical socket the at least two individual members move toward the guide axis.

26. The alignment device of claim 23, wherein the retaining force applying member includes an elastomeric band fit within a groove defined by an external perimeter of the base unit.

27. The alignment device of claim 23, wherein the plurality of standoff features each include a shelf extending into the plurality of standoff features to determine an attachment thickness in combination with the attaching device wherein the attachment thickness is less than a standoff feature thickness.

28. The alignment device of claim 23, further including:
a shelf;
a passage defined by each of the plurality of standoff features;
wherein each of the plurality of standoff features extend from a first standoff feature end to a second standoff feature end;
wherein the shelf defines a surface extending into the passage intermediate the first standoff feature end and the second standoff feature end in the passage;
wherein the attaching device engages the shelf to attach the base unit to the work surface.

29. The alignment device of claim 23, wherein each of the plurality of standoff features extend from the base unit a distance to position the base unit at least a portion of the distance from the work surface.

30. The alignment device claim 23, wherein the retaining force applying member includes a first structure that protrudes from a sidewall that defines the passage.

31. The alignment device of claim 23,
wherein the retaining force applying member is selected from a group consisting of an insert near the passage, a structure protruding into the passage, and an elastomeric band.

32. An alignment device, comprising:
a longitudinal guide portion, having a longitudinal opening including a guide axis;

a spherical portion operably coupled to an end of the longitudinal guide portion;

a base unit, including:

a first portion defining an outer perimeter;

a single deformable spherical socket including at least two fingers extending separately from the first portion for mating with the spherical portion, wherein at least two relief openings are defined as a complete separation between an outer surface and an inner surface of the at least two fingers and the at least two fingers are operable to deform relative to the first portion independently of one another;

an actuating device that surrounds and engages the entire outer perimeter of the spherical socket and operable to substantially symmetrically compress the at least two fingers of the spherical socket, wherein the actuating device is not in direct contact with the spherical portion;

a plurality of standoff features extending from the base unit, wherein the plurality of standoff features are adapted to directly engage a work surface near an opening in the work surface;

a passage defined through each of the plurality of standoff features;

an attaching device operable to pass through the passage and engage the work surface; and a retaining force applying member operable to hold the attaching device relative to the passage at least prior to moving the attaching device relative to the work surface;

wherein the retaining force applying member includes an elastomeric band fit within a groove defined by an external perimeter of the base unit.

33. The alignment device of claim 32, further comprising:

an insert located substantially within the longitudinal opening wherein an outer diameter of the insert fits closely with the longitudinal opening, and an inner diameter is sized to fit closely with a device to be guided;

wherein the insert includes an inner diameter that is sized to fit closely with a biopsy probe.

34. An alignment device, comprising:

a longitudinal guide portion, having a longitudinal opening including a guide axis;

a spherical portion coupled to an end of the longitudinal guide portion;

a base unit, including:

a deformable substantially spherical socket engaging the spherical portion; and a substantially planar portion wherein the deformable spherical socket extends from a first side of the substantially planar portion; and an actuating device surrounding and engaging an outer perimeter of the spherical socket, wherein the actuating device is not in direct contact with the spherical portion;

a number of standoff features attached to the base unit, wherein the standoff features are adapted to directly contact a skull of a subject adjacent to an opening in the skull, wherein the number of standoff features attached to the base unit extend from a second side of the substantially planar portion to position the substantially planar portion a distance away from the skull; and a retaining force applying member that is an elastomeric band across the passage and fit within a groove defined by an external perimeter of the base unit.

\* \* \* \* \*